United States Patent
Cheng et al.

(10) Patent No.: US 12,254,984 B2
(45) Date of Patent: *Mar. 18, 2025

(54) ELECTRONIC DEVICE AND METHOD OF TRAINING CLASSIFICATION MODEL FOR AGE-RELATED MACULAR DEGENERATION

(71) Applicant: Acer Medical Inc., New Taipei (TW)

(72) Inventors: Meng-Che Cheng, New Taipei (TW); Ming-Tzuo Yin, New Taipei (TW); Yi-Ting Hsieh, Taipei (TW)

(73) Assignee: Acer Medical Inc., New Taipei (TW)

( * ) Notice: Subject to any disclaimer, the term of this patent is extended or adjusted under 35 U.S.C. 154(b) by 868 days.

This patent is subject to a terminal disclaimer.

(21) Appl. No.: 17/464,688

(22) Filed: Sep. 2, 2021

(65) Prior Publication Data

US 2022/0392636 A1 Dec. 8, 2022

(30) Foreign Application Priority Data

Jun. 3, 2021 (TW) .................................. 110120195

(51) Int. Cl.
*G16H 50/20* (2018.01)
*G06F 17/18* (2006.01)

(52) U.S. Cl.
CPC ............. *G16H 50/20* (2018.01); *G06F 17/18* (2013.01)

(58) Field of Classification Search
CPC ........ G16H 50/20; G16H 50/70; G06F 17/18; G06V 20/69; G06T 7/00
See application file for complete search history.

(56) References Cited

U.S. PATENT DOCUMENTS

| 11,954,854 B2 * | 4/2024 | Hsu ........................ G16H 50/20 |
| 2023/0222664 A1 * | 7/2023 | Campbell ............ G06V 10/225 351/206 |

FOREIGN PATENT DOCUMENTS

| CN | 112699268 | 4/2021 |
| TW | I702536 | 8/2020 |
| WO | 2019154357 | 8/2019 |

OTHER PUBLICATIONS

Grassmann Felix et al: "A Deep Learning Algorithm for Prediction of Age-Related Eye Disease Study Severity Scale for Age-Related Macular Degeneration from Color Fundus Photography", Ophthalmology, Elsevier, Amsterdam, NL, vol. 125, No. 9, Apr. 10, 2018 (Apr. 10, 2018), pp. 1410-1420, XP085448359. (Year: 2018).*

(Continued)

*Primary Examiner* — John J Lee
(74) *Attorney, Agent, or Firm* — JCIPRNET

(57) ABSTRACT

An electronic device and a method of training a classification model for age-related macular degeneration (AMD) are provided. The method includes the following steps. Training data is obtained. A loss function vector corresponding to the training data is calculated based on a machine learning algorithm, in which the loss function vector includes a first loss function value corresponding to a first stage of AMD and a second loss function value corresponding to a second stage of AMD. A first penalty weight is generated according to a stage difference between the first stage and the second stage. The first loss function value is updated according to the second loss function value and the first penalty weight, so as to generate an updated loss function vector. The classification model is trained according to the updated loss function vector.

9 Claims, 2 Drawing Sheets

(56) References Cited

OTHER PUBLICATIONS

Nec, "Discussion on Intra-UE prioritization and multiplexing", 3GPP TSG RAN WG1 #102-e, Aug. 17-28, 2020, pp. 1-6.
Oppo, "UCI enhancements for URLLC", 3GPP TSG RAN WG1 #100-E, Feb. 24-28, 2020, pp. 1-8.
Oppo, "UCI enhancements for URLLC", 3GPP TSG RAN WG1 #98, Aug. 26-30, 2019, pp. 1-9.
"Search Report of Europe Counterpart Application", issued on Feb. 21, 2022, p. 1-p. 8.
Felix Grassmann PhD et al., "A Deep Learning Algorithm for Prediction of Age-Related Eye Disease Study Severity Scale for Age-Related Macular Degeneration from Color Fundus Photography," Ophthalmology, vol. 125, Sep. 2018, pp. 1410-1420.

* cited by examiner

ELECTRONIC DEVICE AND METHOD OF TRAINING CLASSIFICATION MODEL FOR AGE-RELATED MACULAR DEGENERATION

CROSS-REFERENCE TO RELATED APPLICATION

This application claims the priority benefit of Taiwan application serial no. 110120195, filed on Jun. 3, 2021. The entirety of the above-mentioned patent application is hereby incorporated by reference herein and made a part of this specification.

BACKGROUND

Technical Field

This disclosure relates to an electronic device and a method of training a classification model for age-related macular degeneration.

Description of Related Art

Classifications of age-related macular degeneration (AMD) according to the severity of clinical symptoms are a first stage, a second stage, a third stage, and a fourth stage. Currently, some personnel use an artificial intelligence (AI) model to analyze fundus images so as to classify the severity of the age-related macular degeneration. The personnel may use training data annotated by medical personnel to train the artificial intelligence model. In general, the medical personnel classify the age-related macular degeneration according to the macular area in the fundus image. However, different medical personnel may have different identifications of the macular area. Therefore, the artificial intelligence model trained by the training data annotated by different medical personnel may have an issue of overfitting, thereby reducing the classification accuracy of the artificial intelligence model.

SUMMARY

This disclosure provides an electronic device and a method of training a classification model for age-related macular degeneration, which may train to obtain a classification model for the age-related macular degeneration with high accuracy.

An electronic device for training a classification model for age-related macular degeneration according to the disclosure includes a processor and a transceiver. The processor is coupled to the receiver. The processor is configured to execute the following steps. Training data is obtained through the transceiver. A loss function vector corresponding to the training data is calculated based on a machine learning algorithm, in which the loss function vector includes a first loss function value corresponding to a first stage of the age-related macular degeneration and a second loss function value corresponding to a second stage of the age-related macular degeneration. A first penalty weight is generated according to a stage difference between the first stage and the second stage. The first loss function value is updated according to the second loss function value and the first penalty weight, so as to generate an updated loss function vector. Then, the classification model is trained according to the updated loss function vector.

In an embodiment of the disclosure, the loss function vector further includes a third loss function value corresponding to a third stage of the age-related macular degeneration. The processor is further configured to execute the following steps. A second penalty weight is generated according to a second stage difference between the first classification and the third classification. Then, the first loss function value is updated according to the third loss function value and the second penalty weight, so as to generate the updated loss function vector.

In an embodiment of the disclosure, the second stage difference is greater than the stage difference, and the second penalty weight is greater than the first penalty weight.

In an embodiment of the disclosure, the first penalty weight is proportional to the stage difference.

In an embodiment of the disclosure, the training data includes a fundus image annotated with an age-related macular degeneration stage.

In an embodiment of the disclosure, the loss function vector corresponds to a binary cross-entropy function.

In an embodiment of the disclosure, the processor calculates a normalized probability vector corresponding to the training data based on the machine learning algorithm, generates an one-hot encoding vector corresponding to the age-related macular degeneration stage according to the annotation of the fundus image, and inputs the normalized probability vector and the one-hot encoding vector into the binary cross-entropy function, so as to generate the loss function vector.

In an embodiment of the disclosure, an updated loss function value in the update loss function vector includes the second loss function value and a first product of the first penalty weight.

In an embodiment of the disclosure, the updated loss function value further includes a third loss function and a second product of the second penalty weight.

The method of training the classification model for age-related macular degeneration according to the disclosure includes the following steps. Training data is obtained. A loss function vector corresponding to the training data is calculated based on a machine learning algorithm, in which the loss function vector includes a first loss function value corresponding to a first stage of the age-related macular degeneration and a second loss function value corresponding to a second stage of the age-related macular degeneration. A first penalty weight is generated according to a stage difference between the first stage and the second stage. The first loss function value is updated according to the second loss function value and the first penalty weight, so as to generate an updated loss function vector. Then, the classification model is trained according to the updated loss function vector.

Based on the above, the electronic device of the disclosure may use the penalty weight to update the loss function value of the machine learning algorithm, and use the updated loss function value to train the classification model. The disclosure may prevent over-fitting of the classification model and improve the accuracy of the classification model.

DESCRIPTION OF THE EMBODIMENTS

Figure 1:
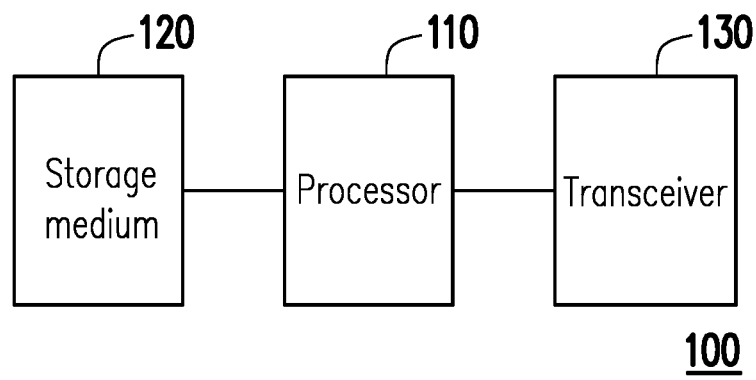
FIG. 1 is a schematic diagram of an electronic device for training a classification model for age-related macular degeneration according to an embodiment of the disclosure.

To make the aforementioned more comprehensible, several embodiments accompanied with drawings are described in detail as follows. The following embodiments are specifically cited as examples which the present invention may be implemented. In addition, wherever possible, elements/components/steps with the same reference numerals in the drawings and the embodiments represent the same or similar components.

A classification model for classifying age-related macular degeneration may be generated based on training data (for example, fundus images with annotations of the age-related macular degeneration stages) annotated by medical personnel. However, the training data with annotations determined by the medical personnel may not necessarily be correct. For example, the medical personnel may classify a first stage of the age-related macular degeneration as a second stage of the age-related macular degeneration. When the classification model is too focused on classifying these easily confused data, the classification model may lose its generalization capability due to overfitting. This disclosure proposes a method of training a classification model for the age-related macular degeneration, which may prevent training to obtain an overfitting classification model.

FIG. 1 is a schematic diagram of an electronic device 100 for training a classification model for age-related macular degeneration according to an embodiment of the disclosure. The electronic device 100 may include a processor 110, a storage medium 120, and a transceiver 130. The classification model may be configured to classify data that is inputted into the first stage, the second stage, the third stage, or the fourth stage of the age-related macular degeneration.

The processor 110 is, for example, a central processing unit (CPU), or other programmable general-purpose or special-purpose micro control unit (MCU), a microprocessor, a digital signal processor (DSP), a programmable controller, an application-specific integrated circuit (ASIC), a graphics processing unit (GPU), an image signal processor (ISP), an image processing unit (IPU), an arithmetic logic unit (ALU), a complex programmable logic device (CPLD), a field programmable gate array (FPGA), or other similar elements, or a combination of the above elements. The processor 110 may be coupled to the storage medium 120 and the transceiver 130, and access and execute multiple modules and various application programs stored in the storage medium 120, so as to execute functions of the electronic device 100.

The storage medium 120 is, for example, any type of fixed or removable random access memory (RAM), a read-only memory (ROM), a flash memory, a hard disk drive (HDD), a solid state drive (SSD), or similar elements, or a combination of the above elements, and is configured to store the multiple modules or the various application programs that may be executed by the processor 110.

The transceiver 130 transmits and receives a signal in a wireless or wired manner. The transceiver 130 may also execute operations such as low noise amplification, impedance matching, frequency mixing, up or down frequency conversion, filtering, amplification, and other similar operations.

The processor 110 may obtain a training data set for training the classification model through the transceiver 130. The training data set may include multiple training data. The training data is, for example, a fundus image annotated with an age-related macular degeneration stage.

Figure 2:
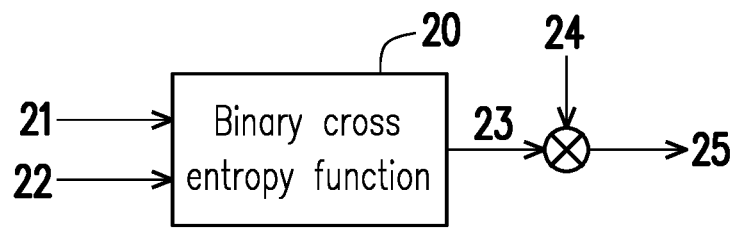
FIG. 2 is a schematic diagram of updating a loss function vector according to an embodiment of the disclosure.

FIG. 2 is a schematic diagram of updating a loss function vector 23 according to an embodiment of the disclosure. The classification model is, for example, a machine learning model. The processor 110 may calculate the loss function vector 23 corresponding to the training data based on a machine learning algorithm. Since the age-related macular degeneration includes the first stage, the second stage, the third stage, and the fourth stage, the loss function vector 23 may include four loss function values respectively corresponding to the first stage, the second stage, the third stage, and the fourth stage. However, the disclosure is not limited thereto. For example, the loss function vector 23 may contain any number of loss function values. In the embodiment, the loss function vector 23 may be expressed as [e(1) e(2) e(3) e(4)], where e(1) is a loss function value corresponding to the first stage, e(2) is a loss function value corresponding to the second stage, e(3) is a loss function value corresponding to the third stage, and e(4) is the a loss function value corresponding to the fourth stage.

A loss function of the machine learning algorithm is, for example, a binary cross entropy function 20. The processor 110 may generate the loss function vector 23 according to the binary cross entropy function 20. Specifically, in the process of training the classification model, a Softmax function of the machine learning algorithm may output a normalized probability vector 21. The normalized probability vector 21 may include four normalized probabilities respectively corresponding to the first stage, the second stage, the third stage, and the fourth stage. However, the disclosure is not limited thereto. For example, the normalized probability vector 21 may contain any number of normalized probabilities. In the embodiment, the normalized probability vector 21 may be expressed as [p(1) p(2) p(3) p(4)], where p(1) is a normalized probability of the first stage, p(2) is a normalized probability of the second stage, p(3) is a normalized probability of the third stage, and p(4) is a normalized probability of the fourth stage. The normalized probability belongs to a closed interval of 0 to 1, as shown in equation (1), where p(j) is a normalized probability of a j-th stage of the age-related macular degeneration.

$$p(j) \in [0,1] \tag{1}$$

On the other hand, the processor 110 may generate a one-hot encoding vector 22 corresponding to the age-related macular degeneration stage according to the annotation of the training data (that is, the fundus image annotated with the age-related macular degeneration stage). The one-hot encoding vector 22 may include four encoding values respectively corresponding to the first stage, the second stage, the third stage, and the fourth stage. However, the disclosure is not limited thereto. For example, the one-hot encoding vector 22 may contain any number of encoding values. In the embodiment, the one-thot encoding vector 22 may be expressed as [c(1) c(2) c(3) c(4)], where c(1) is an encoding value of the first stage, c(2) is an encoding value of the second stage, c(3) is an encoding value of the third stage, and c(4) is an encoding value of the fourth stage. The encoding value may be "0" or "1". The one-hot encoding vector 22 may include one encoding value "1" and three encoding values "0", where the encoding value "1" corresponds to the age-related macular degeneration stage annotated in the training data, and the encoding value "0" corresponds to the age-related macular degeneration stages not annotated in the training data. For example, when the training data is annotated as the third stage, the one-hot encoding vector 22 may be expressed as [0 0 1 0].

After obtaining the normalized probability vector 21 and one-hot encoding vector 22, the processor 110 may input the normalized probability vector 21 and the one-hot encoding vector 22 into the binary cross entropy function 20, so as to generate the loss function vector 23.

In general, two stages with a stage difference that has a smaller absolute value are more difficult to distinguish. Two stages with a stage difference that has a larger absolute value are easier to distinguish. For example, classifying the fundus image as one of the first stage and the second stage is more difficult than classifying the fundus image as one of the first stage and the third stage. In other words, a probability of the first stage being misjudged as the second stage is higher, while a probability of the first stage being misjudged as the third stage is lower. When the classification model is too focused on distinguishing the stages with a smaller stage difference, overfitting may occur. In order to prevent the overfitting of the classification model, the processor 110 may use a penalty weight to update the loss function value of the classification model, and train the classification model according to the updated loss function value.

Specifically, the processor 110 may multiply the loss function vector 23 and a weight matrix 24, so as to generate an updated loss function vector 25, and train the classification model according to the updated loss function vector 25. A size of the updated loss function vector 25 may be the same as a size of the loss function vector 23. Assuming that the loss function vector 23 is expressed as [e(1) e(2) e(3) e(4)], then the processor 110 may calculate the updated loss function vector 25 according to equation (2), where M is the weight matrix 24, and [e(1)' e(2)' e(3)' e(4)'] is the updated loss function vector 25. The updated loss function vector 25 may include an updated loss function e(1)' of the first stage, an updated loss function e(2)' of the second stage, an updated loss function e(3)' of the third stage, and an updated loss function e(4)' of the fourth stage.

$$[e(1)'e(2)'e(3)'e(4)']=[e(1)e(2)e(3)e(4)]M \quad (2)$$

The updated loss function value in the updated loss function vector 25 may be expressed by equation (3), where e(i)' represents an updated loss function value of an i-th stage (or an element of an i-th row of the updated loss function vector 25), and e(j) represents a loss function value of the j-th stage (or an element of a j-th row of the loss function vector 23), a(i,j) represents an error weight corresponding to the i-th stage and the j-th stage, and b(i,j) represents a penalty weight corresponding to the i-th stage and the j-th stage. i or j belong to the closed interval of 1 to 4 (that is, i∈[1,4] and j∈[1,4]). The error weights for the different stages may be the same or different.

$$e(i)'=\Sigma_{i,j}e(j)\cdot(a(i,j)+b(i,j)) \quad (3)$$

As shown in the equation (3), the processor 110 may generate the updated loss function value e (1)' according to the loss function value e(2), the loss function value e(3), or the loss function value e(4). For example, the updated loss function value e(1)' may include a product e(2)·b(1,2) of the loss function value e(2) and a penalty weight b(1,2), a product e(3)·b(1,3) of the loss function value e(3) and a penalty weight b(1,3), and a product e(4)·b(1,4) of the loss function value e(4) and a penalty weight b(1,4).

The processor 110 may calculate the penalty weight b(i, j) corresponding to the i-th stage and the j-th stage according to a stage difference between the i-th stage and the j-th stage (that is, i-j). In an embodiment, the penalty weight b(i, j) may be proportional to the absolute value of the stage difference (that is, i-j) between the i-th stage and the j-th stage, as shown in equation (4). For example, since a stage difference |1-3| between the first stage and the third stage is greater than a stage difference |1-2| between the first stage and the second stage, the penalty weight b(1,3) corresponding to the first stage and the third stage is greater than the penalty weight b(1,2) corresponding to the first stage and the second stage.

$$b(i,j)\propto|i-j| \quad (4)$$

It is assumed that each error weight a(i,j) is equal to 1, and the penalty weight b(i,j) is equal to the stage difference between the i-th stage and the j-th stage multiplied by 0.1 (as shown in equation (5)). Accordingly, the weight matrix 24 in the equation (2) may be expressed as equation (6). The processor 110 may multiply the loss function vector 23 and the weight matrix 24, so as to generate the updated loss function vector 25. After obtaining the updated loss function vector 25, the processor 110 may train the classification model for the age-related macular degeneration according to the updated loss function vector 25.

$$b(i, j) = 0.1 \cdot |i - j| \quad (5)$$

$$M = \begin{bmatrix} 0 & 1+0.1 & 1+0.2 & 1+0.3 \\ 1+0.1 & 0 & 1+0.1 & 1+0.2 \\ 1+0.2 & 1+0.1 & 0 & 1+0.1 \\ 1+0.3 & 1+0.2 & 1+0.1 & 0 \end{bmatrix} \quad (6)$$

Figure 3:
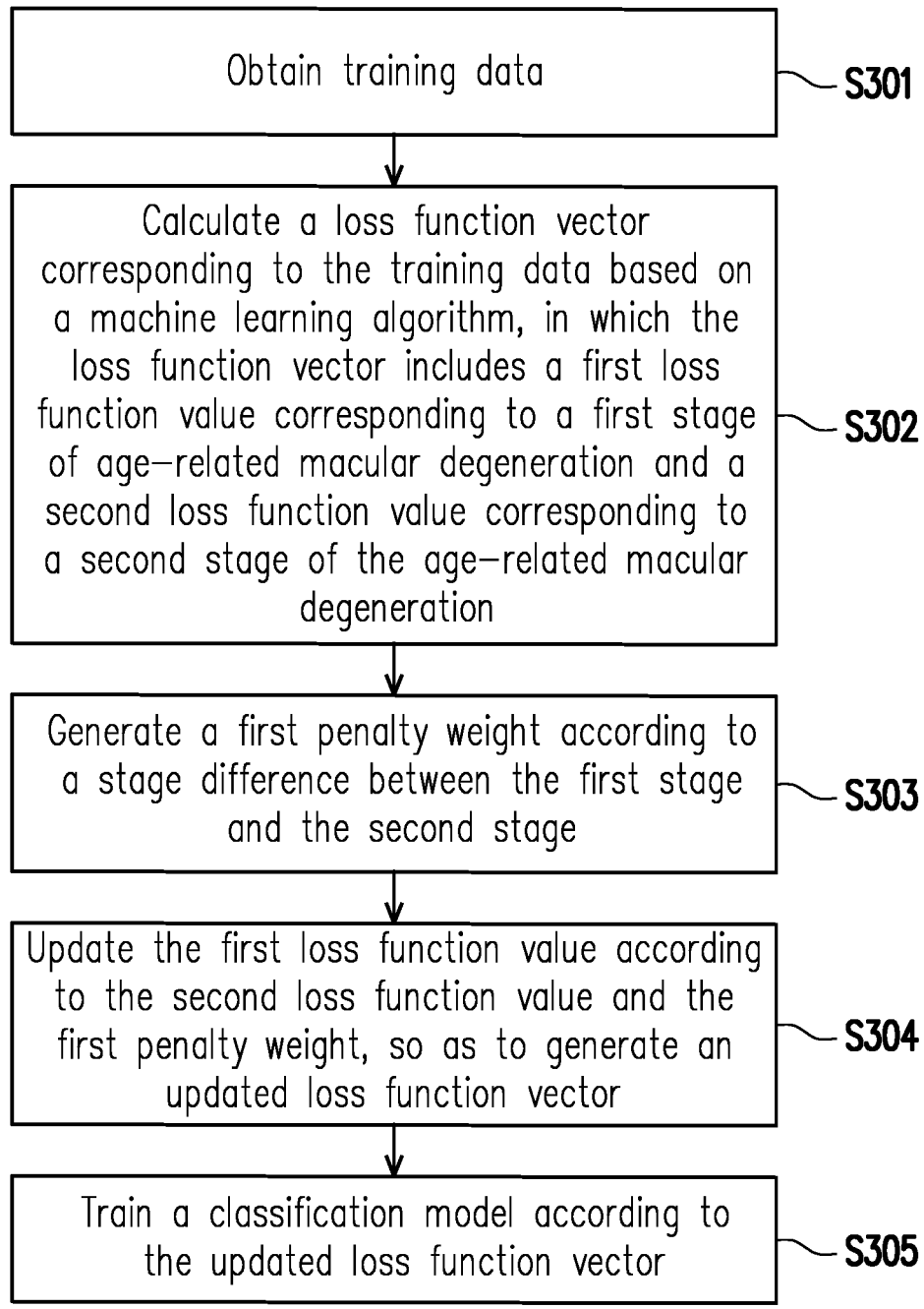
FIG. 3 is a flowchart of a method of training a classification model for age-related macular degeneration according to an embodiment of the disclosure.

FIG. 3 is a flowchart of a method of training a classification model for age-related macular degeneration according to an embodiment of the disclosure. The method may be implemented by the electronic device 100 shown in FIG. 1. In Step S301, the training data is obtained. In Step S302, the loss function vector corresponding to the training data is calculated based on the machine learning algorithm. The loss function vector includes a first loss function value corresponding to the first stage of the age-related macular degeneration and a second loss function value corresponding to the second stage of the age-related macular degeneration. In Step S303, a first penalty weight is generated according to the stage difference between the first stage and the second stage. In Step S304, the first loss function value is updated according to the second loss function value and the first penalty weight, so as to generate the updated loss function vector. In Step S305, the classification model is trained according to the updated loss function vector.

In summary, the electronic device of the disclosure may use the penalty weight to update the loss function value of the machine learning algorithm. The electronic device may use the loss function value of another classification to update the loss function value of a specific classification. When the other classification and the specific classification are classifications that are easily confused, the electronic device gives the other classification a smaller penalty weight. When the other classification and the specific classification are classifications that are not easily confused, the electronic device gives the other classification a greater penalty weight. In this way, the classification model trained by the updated loss function value will not be over-fitting due to being too focused on distinguishing the easily confused classifications. Accordingly, the electronic device of the disclosure may improve the accuracy of the classification model.

Although the disclosure has been described with reference to the above-mentioned embodiments, it is not intended to be exhaustive or to limit the disclosure to the precise form or to exemplary embodiments disclosed. It is apparent to one of ordinary skill in the art that modifications to the described embodiments may be made without departing from the spirit and the scope of the disclosure. Accordingly, the scope of the disclosure is defined by the claims appended hereto and their equivalents in which all terms are meant in their broadest reasonable sense unless otherwise indicated.

What is claimed is:

1. An electronic device for training a classification model for age-related macular degeneration, comprising:
   a transceiver; and
   a processor, coupled to the transceiver, wherein the processor is configured to:
   obtaining training data through the transceiver;
   calculate a loss function vector corresponding to the training data based on a machine learning algorithm, wherein the loss function vector comprises a first loss function value corresponding to a first stage of the age-related macular degeneration and a second loss function value corresponding to a second stage of the age-related macular degeneration;
   generate a first penalty weight according to a stage difference between the first stage and the second stage, wherein the first penalty weight is proportional to the stage difference;
   update the first loss function value according to the second loss function value and the first penalty weight, so as to generate an updated loss function vector; and
   train the classification model according to the updated loss function vector.

2. The electronic device according to claim 1, wherein the loss function vector further comprises a third loss function value corresponding to a third stage of the age-related macular degeneration, wherein the processor is further configured to:
   generate a second penalty weight according to a second stage difference between the first stage and the third stage; and
   update the first loss function value according to the third loss function value and the second penalty weight, so as to generate the updated loss function vector.

3. The electronic device according to claim 2, wherein the second stage difference is greater than the stage difference, and the second penalty weight is greater than the first penalty weight.

4. The electronic device according to claim 2, wherein an updated loss function value in the update loss function vector comprises the second loss function value and a first product of the first penalty weight.

5. The electronic device according to claim 4, wherein the updated loss function value further comprises the third loss function and a second product of the second penalty weight.

6. The electronic device according to claim 1, wherein the training data comprises a fundus image annotated with an age-related macular degeneration stage.

7. The electronic device according to claim 6, wherein the loss function vector corresponds to a binary cross entropy function.

8. The electronic device according to claim 7, wherein the processor calculates a normalized probability vector corresponding to the training data based on the machine learning algorithm, generates an one-hot encoding vector corresponding to the age-related macular degeneration stage according to the annotation of the fundus image, and inputs the normalized probability vector and the one-hot encoding vector into the binary cross-entropy function, so as to generate the loss function vector.

9. A method of training a classification model for age-related macular degeneration, comprising:
   obtaining training data;
   calculating a loss function vector corresponding to the training data based on a machine learning algorithm, wherein the loss function vector comprises a first loss function value corresponding to a first stage of the age-related macular degeneration and a second loss function value corresponding to a second stage of the age-related macular degeneration;
   generating a first penalty weight according to a stage difference between the first stage and the second stage, wherein the first penalty weight is proportional to the stage difference;
   updating the first loss function value according to the second loss function value and the first penalty weight, so as to generate an updated loss function vector; and
   training the classification model according to the updated loss function vector.

* * * * *